US012766245B2

(12) United States Patent
Mahadev et al.

(10) Patent No.: US 12,766,245 B2
(45) Date of Patent: Oct. 20, 2026

(54) SINGLE USE DISPOSABLE TIME INDICATION DEVICES

(71) Applicant: CareFusion 303, Inc., San Diego, CA (US)

(72) Inventors: Shwetha Mahadev, Bangalore (IN); Abin Austin, Thrissur (IN); Shraya Sajjanar, Dharwad (IN)

(73) Assignee: CAREFUSION 303, INC., San Diego, CA (US)

( * ) Notice: Subject to any disclaimer, the term of this patent is extended or adjusted under 35 U.S.C. 154(b) by 940 days.

(21) Appl. No.: 17/978,613

(22) Filed: Nov. 1, 2022

(65) Prior Publication Data

US 2023/0166025 A1 Jun. 1, 2023

Related U.S. Application Data

(60) Provisional application No. 63/283,756, filed on Nov. 29, 2021.

(51) Int. Cl.

*A61M 5/142* (2006.01)
*A61M 5/32* (2006.01)
*A61M 39/14* (2006.01)

(52) U.S. Cl.

CPC .......... *A61M 5/142* (2013.01); *A61M 5/3204* (2013.01); *A61M 39/14* (2013.01); *A61M 2005/14208* (2013.01); *A61M 2205/3389* (2013.01); *A61M 2205/3396* (2013.01)

(58) Field of Classification Search

None

See application file for complete search history.

(56) References Cited

U.S. PATENT DOCUMENTS

| | | | | |
|---|---|---|---|---|
| 5,535,771 | A * | 7/1996 | Purdy | A61M 39/0606 604/905 |
| 7,981,381 | B2 * | 7/2011 | Lurvey | G01N 21/78 422/50 |
| 8,137,303 | B2 | 3/2012 | Stout et al. | |
| 8,388,131 | B2 | 3/2013 | Heacock et al. | |
| 10,603,481 | B2 * | 3/2020 | Avula | A61L 2/18 |
| 2007/0293822 | A1 * | 12/2007 | Crawford | G09F 3/0291 604/175 |
| 2008/0132877 | A1 * | 6/2008 | McKinnon | A61M 39/045 604/246 |

(Continued)

FOREIGN PATENT DOCUMENTS

EP 2968890 A1 1/2016

OTHER PUBLICATIONS

International Search Report and Written Opinion for Application No. PCT/US2022/050479, dated Feb. 23, 2023, 17 pages.

*Primary Examiner* — Jonathan M Peo

(74) *Attorney, Agent, or Firm* — MASCHOFF BRENNAN

(57) ABSTRACT

An IV disposable time indication device includes one of a tube and a slot containing a volume of gel, wherein the gel is configured to evaporate at a determined rate of time upon activation by exposure to ambient air. A seal is configured to prevent contact of the gel with ambient air. One or more time indicators are disposed on the device, wherein evaporation of the gel is configured to provide a visual indication of a passage of time after activation. Methods of operating an IV disposable time indication device are also provided.

19 Claims, 8 Drawing Sheets

(56) References Cited

U.S. PATENT DOCUMENTS

| | | | | |
|---|---|---|---|---|
| 2009/0008393 | A1* | 1/2009 | Howlett | A61M 39/20 220/380 |
| 2016/0089530 | A1 | 3/2016 | Sathe | |
| 2019/0060615 | A1 | 2/2019 | Skeele et al. | |

* cited by examiner

SINGLE USE DISPOSABLE TIME INDICATION DEVICES

CROSS-REFERENCE TO RELATED APPLICATIONS

This application claims the benefit of priority under 35 U.S.C. § 119 to U.S. Provisional Patent Application Ser. No. 63/283,756, entitled "SINGLE USE DISPOSABLE TIME INDICATION DEVICES," filed on Nov. 29, 2021, the entirety of which is incorporated herein by reference.

TECHNICAL FIELD

The present disclosure generally relates to intravenous (IV) set devices, in particular single use disposable time indication devices.

BACKGROUND

Typical infusion or intravenous (IV) sets are constructed by joining multiple translucent polymeric tubing segments to multiple polymeric components, many of which are also translucent. These IV sets are then used with infusion pumps or gravity systems to provide fluids to a user, such as a patient. However, an IV set and/or individual IV components typically have both a predetermined shelf life (e.g., 3-5 years storage time) and a predetermined use life (e.g., 24 hours, 72 hours, 96 hours, 7 days). Also, IV disposables are limited or restricted use products that can transmit contaminants and diseases, or any sort of infection if reused or used beyond the recommended period. In particular, once an IV set/component is removed from its packaging and put into use, the IV set/component should only be used for a length of time up to the use life, after which time the IV set/component should be changed out. The time of use may be determined by healthcare regulations, the type(s) of drugs, medications or substances that are being infused through the IV set/component, and the types of materials used to make the IV set/component.

Currently, there is no good way to alert the clinician when an IV line/component should or needs to be changed. Typically, when the IV set/component is put into use, it is up to the clinician to chart or note the start time of the IV set/component use. However, in the hectic environment of some medical settings, the clinician may not have time to chart or note the start time. In addition, it may not be clear which use life time period a particular IV set/component in use requires. Further, when a clinician does determine that an IV set/component change is required, the action of changing the IV set/component is time and labor intensive, requiring locating the set/component, determining the medication being provided by the set/component and/or manually labeling IV lines. If the patient has several IV lines, such as in the intensive care unit (ICU), the task of finding and changing out the correct IV set/component can be time consuming.

For these reasons, it is desirable to provide devices and methods for providing IV sets/component with built-in timers that visually show how much life is left of the associated IV set/component, thus giving the clinician the ability to determine the remaining use life of any IV set/component, to provide ample time for the clinician to make preparations for changing the IV set/component and to provide a clear indication to the clinician that the IV set/component has reached its maximum use life.

SUMMARY

In one or more embodiments, an IV disposable time indication device comprises: a tube containing a volume of gel, wherein the gel is configured to evaporate at a determined rate of time upon activation by exposure to ambient air; a seal configured to prevent contact of the gel with ambient air; and one or more time indicators, wherein evaporation of the gel is configured to provide a visual indication of a passage of time after activation.

In one or more embodiments, an IV disposable time indication device comprises: a cap configured to be coupled to an IV component, the cap comprising: a cavity having a base surface; a slot disposed in the base surface; a volume of gel disposed in the slot, wherein the gel is configured to evaporate at a determined rate of time upon activation by exposure to ambient air; and one or more time indicators; and a seal configured to prevent contact of the gel with ambient air, wherein evaporation of the gel is configured to provide a visual indication of a passage of time after activation.

In one or more embodiments, a method of operating an IV disposable time indication device comprises: placing an IV component into use for an IV infusion process; removing a seal from the IV disposable time indication device coupled to the IV component; exposing a gel within the IV disposable time indication device to ambient air; visually identifying a level of the gel relative to one or more time indicator markings disposed adjacent to the gel; and determining the remaining use life of the IV component based on the time indicator marking closest to the identified level of gel.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
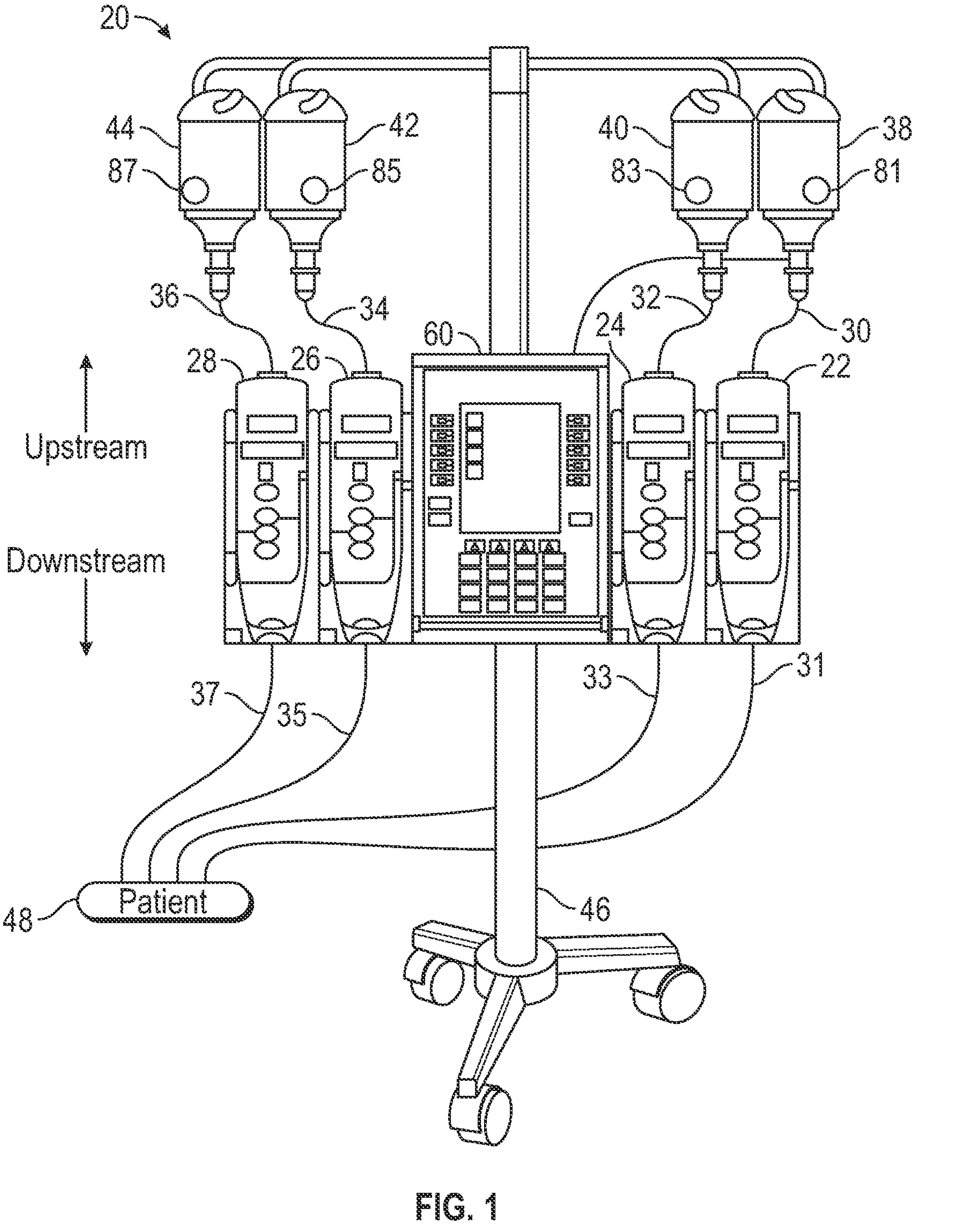
FIG. 1 depicts a perspective view of an example patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, table top, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or other fluids. The infusion pumps 22, 24, 26, and 28 are controlled by a pump control unit 60.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Typical infusion sets may also be gravity sets that do not require use of an infusion pump. For example, any of fluid supplies 38, 40, 42, and 44 may be directly connected to the patient 48 via a gravity IV set, wherein gravity causes the fluid to flow through the infusion set and into the patient 48 without the aid of a pump.

Figure 2A:
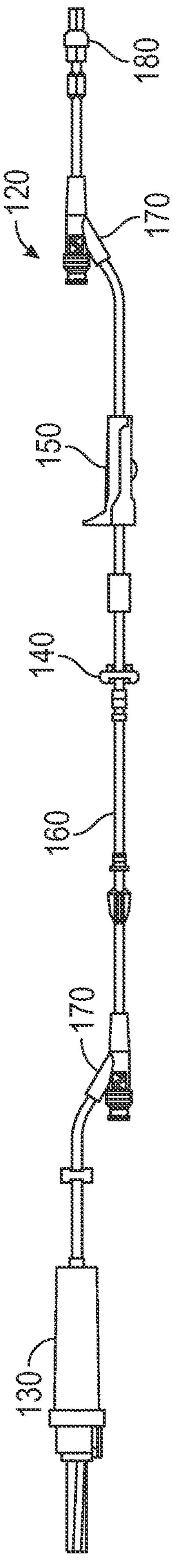
FIGS. 2A-2C are top views of example IV sets and extension sets.
Figure 2C:
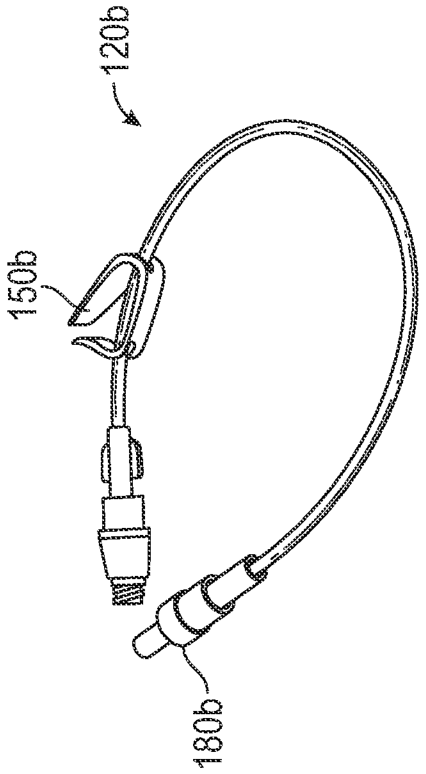
Figure 2B:
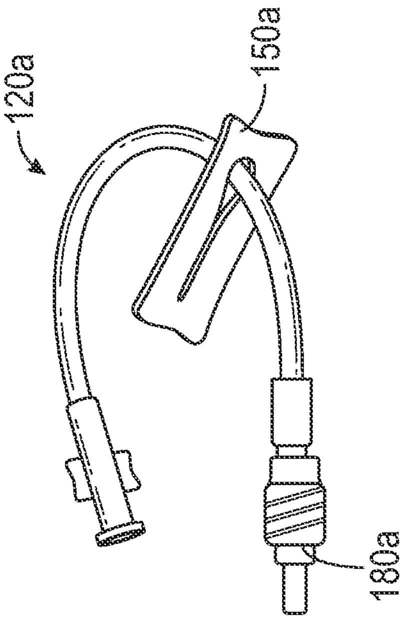

Typically, medical fluid administration sets have more parts than are shown in FIG. 1, such as those shown in FIGS. 2A-2C. Infusion sets may be formed from any combination of infusion components and tubing. Typically, the infusion components and tubing are disposable products that are used once and then discarded. The infusion components and tubing may be formed from any suitable material (e.g., plastic, silicone, rubber), many or all of which are clear or translucent so that the fluid flow or levels inside can be seen.

As shown in FIGS. 2A, an infusion set 120 may include a drip chamber 130, a check valve 140, a flow controller 150 (e.g., roller clamp) and a pump segment 165 connected together by tubing 160. The infusion set 120 may also include a Y-site 170 having a Y-shaped junction with a needleless port 175, as well as a luer lock connector 180 at the end of the infusion set 120. The luer lock connector 180 may be used for connection to a catheter inserted into a patient, for example. The infusion set 120 may include additional infusion components and may be formed of any combination of components and the tubing 160. For example, substituting a length of tubing 160 for the pump segment 165 of infusion set 120 can change the infusion set 120 from a pump IV set to a gravity IV set.

As shown in FIG. 2B, an IV extension set **120*a* may be used to connect any two infusion components or devices, such as IV sets, infusion pumps, syringe pumps and the like. IV extension set 120*a* includes a luer lock connector 180*a* and a flow controller 150*a*. Similarly, as shown in FIG. 2C, another IV extension set 120*b* includes a luer lock connector 180*b* and a flow controller 150*b***.

In general, almost all single use disposable IV devices (e.g., needleless connector, catheter) have a desired time limit for usage. In aspects of the disclosure, the subject technology provides a timer device as part of the IV set/component. For example, the IV set/component may have a built-in timer indicator that visually shows the remaining use life of the IV set/component. This provides for accurate use of IV sets/components, eliminating both too frequent changing of IV sets/components (e.g., clinician not sure when IV set/component use life is up and changes IV set/component too frequently, wasting the remaining use life hours of the replaced IV set/component) and overuse of an IV set/component past the use life of the IV set/component (e.g., clinician not sure when IV set/component use life is up and changes IV set/component too infrequently, possibly causing medical, administrative and legal issues).

Figure 3:
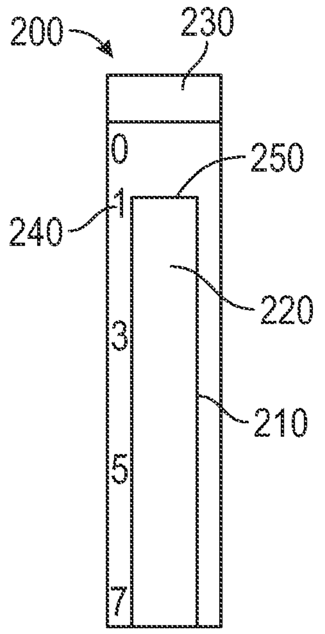
FIG. 3 is a front view of a single use disposable time indication device, according to aspects of the disclosure.

In aspects of the disclosure as shown in FIG. 3, a single use disposable time indication device 200 is provided. Time indication device 200 may include a tube 210 containing a gel 220 that evaporates over time when exposed to air, such as carbon dioxide, oxygen or any combination of gases in the ambient air where the time indication device 200 is being used. The time indication device 200 also may include a seal 230 for sealing the gel 220 in the tube 210. For example, the seal 230 may be the packaging for an IV set/component. Here, the time indication device 200 may start timing when the IV set/component of which the time indication device 200 is associated is removed from its seal 230 (e.g., vacuum sealed packaging), thus exposing the time indication device 200 to the air. As another example, the seal 230 may be a peel off cover over the opening of the tube 210. Here, the time indication device 200 may start timing when the seal (e.g., peel off cover) is removed, again exposing the time indication device 200 to the air.

In aspects of the disclosure, the time indication device 200 provides an indication of time elapsed after its activation (e.g., seal 230 removed). Thus, the rate of evaporation of the gel 220 in the tube 210 is a function of time. Also, the volume of gel 220 in the tube 210 is a function of time.

In aspects of the disclosure, as shown in FIG. 3, the time indication device 200 may also include time indicators 240. For example, the time indicators 240 may be marks and/or text (e.g., numbers, words, symbols) disposed on the tube 210. Thus, the associated time period may be indicated by the time indicators 240, such as word descriptions of the time period (e.g., day 1, day 2, day 3, day 4) or simply numbers by themselves (e.g., 1, 3, 5). For example, when the gel 220 is activated by exposure to air, the gel 220 may be visible through the tube 210 to a level 250 marked by a first time indicator 240 (e.g., full, 0 day). As the gel 220 evaporates over a time period (e.g., 24 hours, 1 day), the gel level 250 visible through the tube 210 recedes to a second time indicator 240. The time indication device 200 may include any number of time indicators 240 in order to indicate a desired use life time period (e.g., 24 hours, 72 hours, 96 hours, 7 days) for the associated IV set/component.

Thus, as the gel 220 continues to evaporate, the gel level 250 continues to recede along the tube 210 through the remaining time indicators 240, until the gel 220 evaporates enough (e.g., fully evaporated) so that the gel level 250 is aligned with a final time indicator 240. For example, as shown in FIG. 3, the time indication device 200 may be a seven day device having five time indicators 240, where the first time indicator 240 indicates that full use life of the IV set/component remains (e.g., just activated and/or placed in service), while the second through fifth time indicators 240 each indicate a number of days that have passed since the time indication device 200 was activated (e.g., 1 day, 3 days, 5 days, 7 days). Here, when the final time period expires (e.g., 7 days), the gel 220 may be fully evaporated and thus no longer visible, or there may still be some residual gel 220 in the tube 210 at a gel level 250 equal to or less than the final time indicator 240.

Thus, with a quick glance at the gel level 250 of a time indication device 200 for an associated IV set/component that is in use, a clinician can easily and quickly determine how much use life remains for the IV set/component. For example, if the gel level 250 shown in FIG. 3 is half way between the fourth and fifth time indicators 240, the clinician can quickly determine that the IV set/component is within its last day of use life and can make preparations for replacing the IV set/component within the remaining one day time period. Here, the clinician can put in an order for a replacement IV set/component, check the room or local inventory to make sure a replacement IV set/component is on hand, enter instructions for the change of shift that an IV se/component will need to be replaced soon, and/or any other preparations that may be necessary.

In aspects of the disclosure, the gel level 250 in conjunction with the time indicators 240 allows the clinician to know if the IV set/component has enough usage time left prior to starting an infusion therapy that would exceed the life of the IV set/component. In this case, the clinician can change the IV set/component prior to starting the IV therapy to avoid having to interrupt the therapy to replace the IV set/component.

In aspects of the disclosure, an IV set timer device may have any suitable form or format. For example, instead of the rectangular form shown in time indication device 200, the time indication device may be a circular patch, a square patch or any other geometric shaped patch where the gel level visibly recedes over time.

In aspects of the disclosure, legends and/or instructions may be disposed on any suitable portion of the time indication device 200. For example, legends and/or instructions may be printed on top of the tube 210 where the recession of the gel level 250 occurs underneath and/or around the legend/instruction, may be printed on outer portions of the time indication device 200 (e.g., not over the tube 210), formed underneath the tube 210 so that the legend/instruction becomes visible when the gel 220 recedes past that portion of the tube 210, or any other suitable form.

Figure 4:
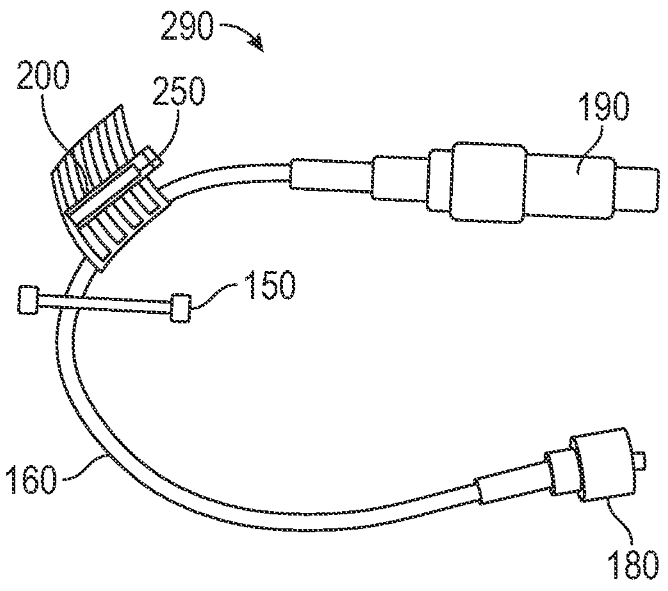
FIG. 4 depicts a perspective view of an IV set with a single use disposable time indication device, according to aspects of the disclosure.

FIG. 4 shows an example IV extension set 290 having a needless connector 190, a flow controller 150, a luer lock connector 180 and IV tubing 160. IV extension set 290 also includes a time indication device 200 affixed to the IV tubing 160 as a label, the time indication device 200 having gel level 250 that recedes over time after being activated. Here, the time indication device 200 may be affixed to the IV tubing 160 as a label if there are no infusion components within the IV extension set 290 that are suitable (e.g., large enough, allowed to be partially obscured) to include the time indication device 200.

According to aspects of the disclosure, the seal 230 may be a vacuum sealed or airtight packaging and when the IV extension set 290 is removed from the packaging (e.g., removed from seal 230), the time indication device 200 may be automatically activated upon exposure to ambient air and start its timing function. According to aspects of the disclosure, the seal 230 may be a peel off label or covering and when the IV extension set 290 is put in use, the seal 230 is peeled off (e.g., removed) from the time indication device 200, which then may be activated upon exposure to ambient air and start its timing function.

Figure 5:
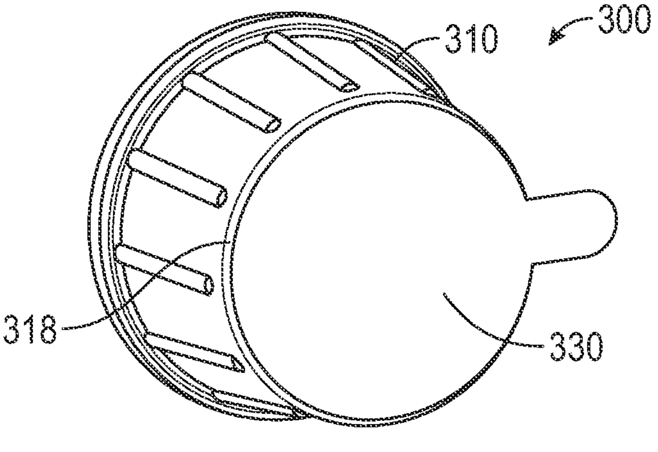
FIG. 5 depicts a perspective view of a single use disposable time indication device, according to aspects of the disclosure.
Figure 6:
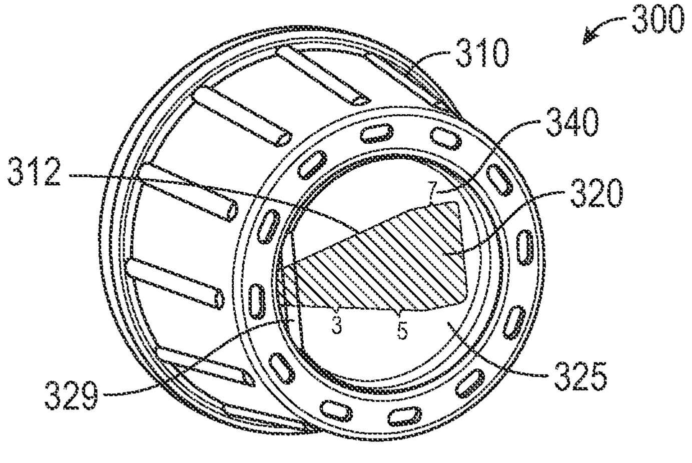
FIG. 6 depicts a perspective view of the single use disposable time indication device of FIG. 5 without a cover seal, according to aspects of the disclosure.
Figure 7:
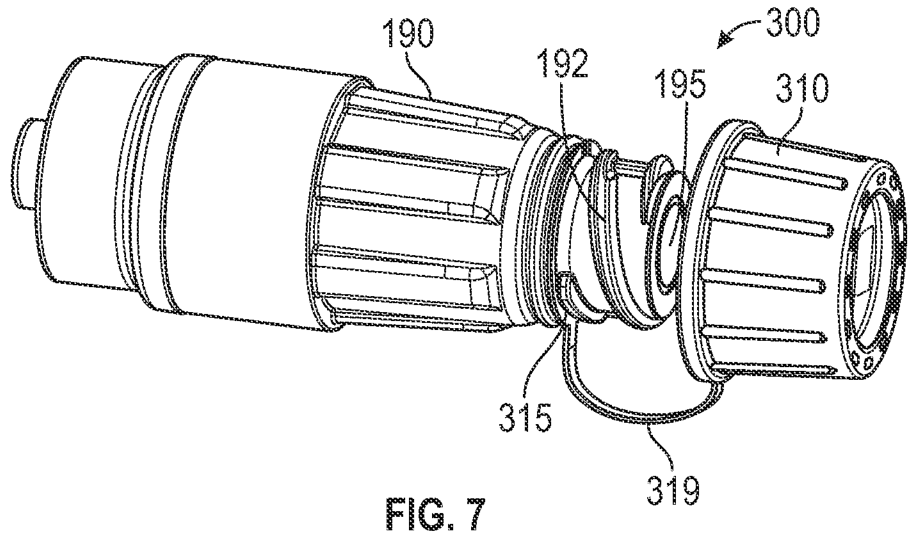
FIG. 7 depicts a perspective view of an IV connector with a single use disposable time indication device, according to aspects of the disclosure.

In aspects of the disclosure as shown in FIGS. 5 to 10, a single use disposable time indication device 300 is provided. Time indication device 300 may include a cap 310 configured as a disinfecting cap for use with an IV set component, such as a needleless connector 190 having a port 195 as shown in FIG. 7. For example, the cap 310 may disinfect the needleless port 195 with a sterilized 70% IPA solution, providing a >4-log (99.99%) reduction in bacteria within one minute of application. Here, the cap 310 may be used to protect the needleless port 195 and maintains a physical barrier to contamination for up to seven days.

In aspects of the disclosure, the cap 310 may be a completely separable component as shown in FIGS. 5 and 6. However, detachable sterile caps typically must be made readily available in the patient care area. Thus, if the clinician forgets to cap the connector back after use, the connector could go uncapped and increase the risk of intraluminal contamination. Accordingly, in aspects of the disclosure as shown in FIG. 7, the cap 310 may include an attachment member 315 configured to couple with an IV component (e.g., needleless connector 190) and a tether 319 coupling the cap 310 to the attachment member 315. Thus, the attachment member 315 and tether 319 keep the cap 310 attached to the needless connector 190 when the cap 310 is not mated with the needless connector 190, which may eliminate or minimize the risk of losing the cap 310 during use.

For example, the cap 310 may need to be unscrewed multiple times a day over a 7 day use life period so that medications can be injected into the port 195, after which the cap 310 needs to be screwed back on to the needleless connector 190 each time in order to protect and/or disinfect the port 195. Accordingly, when the cap 310 is always connected to the needleless connector 190 by the attachment member 315 and tether 319, the attached cap 310 provides a visible reminder to the clinician when the medication injection is complete. In addition, the attached cap 310 cannot be set down and forgotten, nor will the attached cap 310 likely be dropped onto an unsterile surface or lost.

The cap 310 may include a slot 312 disposed in a base surface 314 of a cavity 316, the slot 312 configured to hold a volume of a gel 320 that evaporates over time when exposed to air, such as carbon dioxide, oxygen or any combination of gases in the ambient air where the time indication device 300 is being used. The time indication device 300 also may include a cap closer 325 configured to fit within the cavity 316 and to hold the gel 320 in the slot 312. The cap closer 325 may be configured to provide a snug and/or sealing fit with a majority of the wall 317 of the cavity 316. The cap closer 325 may also have a vent portion 327 that does not contact the wall 317, thus providing an air passageway 329 between the gel 320 in the slot 312 and the ambient air. The cap closer 325 may be clear or a transparent color such that the gel 320 and the slot 312 are visible through the cap closer 325.

The time indication device 300 may also include a seal 330 (e.g., peel off hermetic seal) for sealing the air passageway 329 of the cap closer 325, thus preventing evaporation of the gel 320 from the slot 312. For example, the seal 330 may be a peel off cover disposed over a top surface 318 of the cap 310 and completely covering the cap closer 325 and the air passageway 329. Here, the time indication device 300 may start timing (e.g., is activated) when the seal 330 (e.g., peel off cover) is removed, thus exposing the gel 320 in the slot 312 of the time indication device 300 to the ambient air through the air passageway 329. In aspects of the disclosure, the seal 330 may be removed from the cap 310 upon removing the cap 310 from its packaging. In aspects of the disclosure, the seal 330 may be removed from the cap 310 once the cap is screwed or threaded on to the needleless connector 190 to cover the port 195.

In aspects of the disclosure, as shown in FIG. 6, the time indication device 300 may also include time indicators 340. For example, the time indicators 340 may be marks and/or text (e.g., numbers, words, symbols) disposed on the base surface 314 of the cavity 316 at specific points along the slot 312. Thus, the associated time period may be indicated by the time indicators 340, such as word descriptions of the time period (e.g., day 1, day 2, day 3, day 4) or simply numbers by themselves (e.g., 3, 5, 7).

Figure 8A:
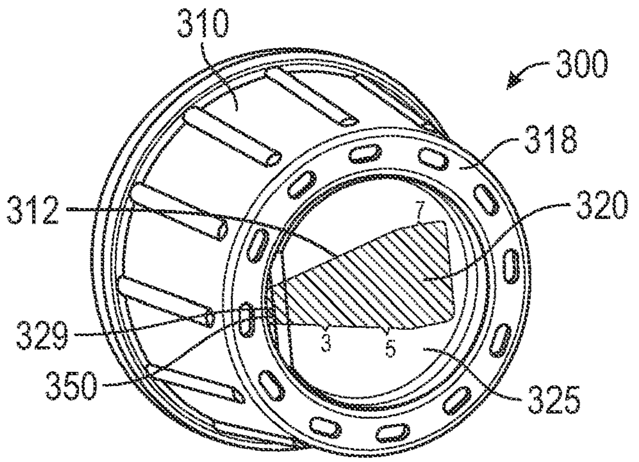
FIGS. 8A to 8C depict perspective views of the single use disposable time indication device of FIG. 6 at various times of use, according to aspects of the disclosure.
Figure 8B:
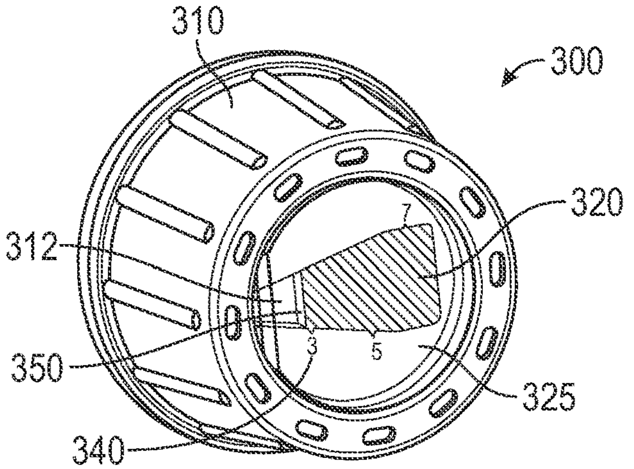
Figure 8C:
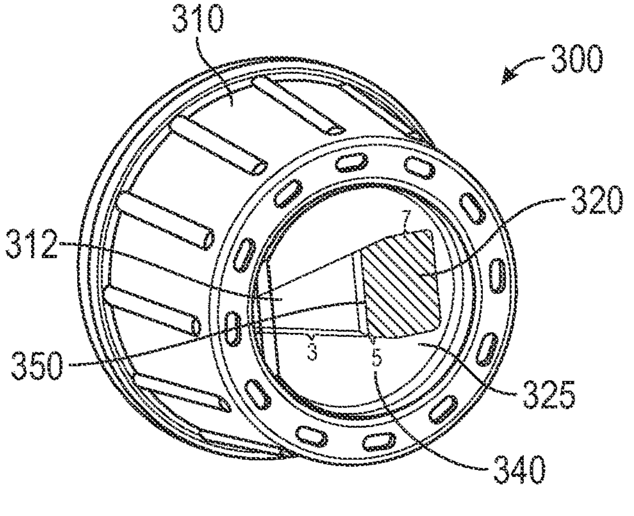

For example, as shown in FIG. 8A, when the gel 320 is activated by exposure to air through the air passageway 329, the gel 320 may be visible through the cap closer 325 to show a gel level 350 indicating the slot 312 is full of gel 320. Then, a reduction in the volume of the gel 320 in the slot 312 indicates the passing time from the activation of the cap 310. As shown in FIG. 8B, when the gel 320 evaporates over a first time period (e.g., 3 days), the gel level 350 visible through the cap closer 325 recedes in the slot 312 to a first time indicator 340 (e.g., 3). As the gel 320 evaporates over a second time period (e.g., 2 more days for a total of 5 days) as shown in FIG. 8C, the gel level 350 visible through the cap closer 325 recedes in the slot 312 to a second time indicator 340 (e.g., 5).

The time indication device 300 may include any number of time indicators 340 in order to indicate a desired use life time period (e.g., 24 hours, 72 hours, 96 hours, 7 days) for the cap 310 itself or for an associated IV set/component (e.g., IV extension set 290, needleless connector 190). For the example shown in FIGS. 8A to 8C, the use life of the cap 310 may be 7 days and there may still be some gel 320 visible to the right of the time indicator 340 marked as a 7 when the 7 days have passed. In aspects of the disclosure, the final time indicator 340 indicating the maximum use life may be located at the end of the slot 312, in which case little or no gel 320 would be visible once the maximum use life time period had passed.

Figure 9:
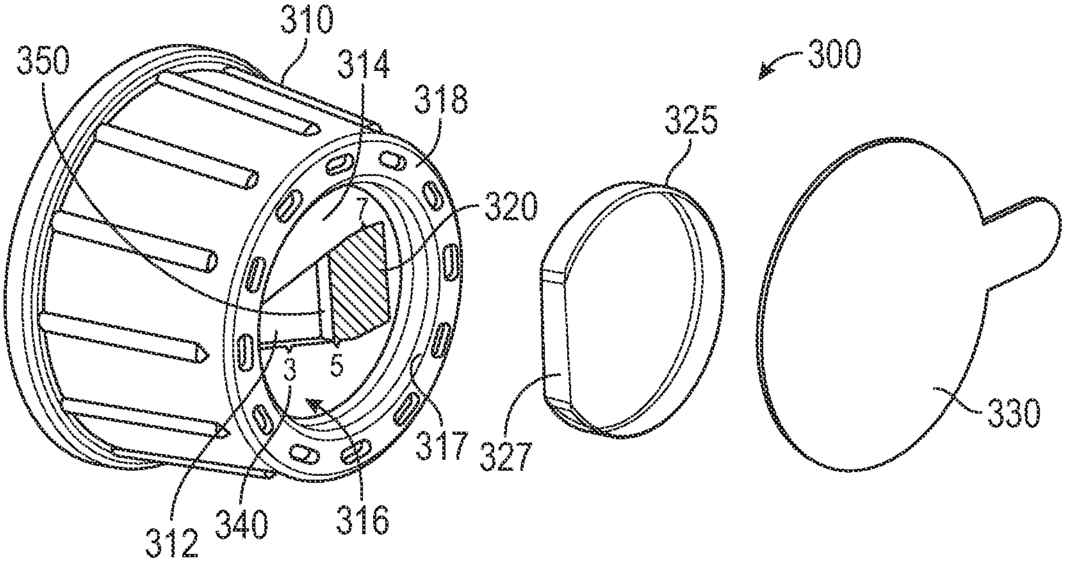
FIG. 9 depicts an exploded perspective view of the single use disposable time indication device of FIG. 6, according to aspects of the disclosure.

FIG. 9 shows an exploded view of the time indication device 300. Each of the components of the time indication device 300, including the cap 310, the cap closer 325 and the seal 330 may be easily molded or manufactured components. Similarly, the cap 310, attachment member 315 and tether 319 may be molded as a single integral component.

Figure 10:
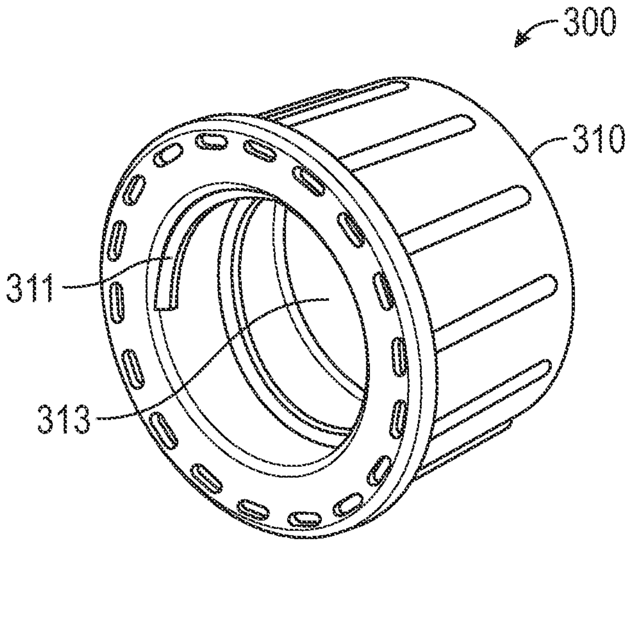
FIG. 10 depicts a rear perspective view of the single use disposable time indication device of FIG. 6, according to aspects of the disclosure.

FIG. 10 shows the underside of the cap 310. For example, threads 311 may be configured to mate with any threaded connector, such as with threads 192 of the needleless connector 190 shown in FIG. 7. An internal surface 313 of the base 314 of the cavity 316 may include a disinfectant that contacts and disinfects and/or sterilizes the port 195 when the cap 310 is fully mated with the needleless connector 190.

In aspects of the disclosure, the time indication device 200, 300 may be added to an IV set component during manufacturing and packaging of the IV set. In aspects of the disclosure, the time indication device 200, 300 may be provided separately on a roll, a sheet, in individual packages or any other suitable storage device, where the clinician or user applies the time indication device 200, 300 to some portion of the IV set when the IV set is put into use.

For example, a roll or sheet of time indication devices 200 with seals 230, or a box or bag of time indication devices 300 with seals 330 may be on hand in a medical treatment area. Here, when a new IV set or an IV set component is put into use, the clinician may remove a time indication device 200 from the roll or sheet, thus exposing an adhesive back surface, and apply the adhesive surface to an IV set component, then peel off the seal 230 to activate the time indication device 200. Similarly, the clinician may remove a time indication device 300 from the container or bag and screw the cap 310 on to an IV set connector, then peel off the seal 330 to activate the time indication device 300.

As another example, a time indication device 200 may be sealed in an airtight or vacuum sealed individual package. Here, when a new IV set or new single IV set component is put into use, the clinician may remove the time indication device 200 from the sealed individual package, exposing the gel 220 in the tube 210 to the air to activate the time indication device 200, peel off a back cover to expose an adhesive back surface, and apply the adhesive surface to an IV set component In aspects of the disclosure, the time indication device 200 may be applied by an applicator device (e.g., applicator gun). For example, a handheld applicator device (e.g., like a tape gun or label applicator) may be used by the clinician to apply time indication devices 200 to IV set components as needed. Here, the applicator device may lift the time indication device 200 from a backing roll to expose an adhesive surface of the time indication device 200, and peel off the seal 230 to activate the time indication device 200 upon application from the applicator device to the IV set component. As another example, the applicator device may be a robotic or machine portion of a manufacturing system or assembly system, where the a time indication device 200, 300 is automatically applied or coupled to an IV set component during manufacturing, assembly or packaging of an IV set.

In aspects of the disclosure, sample evaporation calculations are provided. For example, the amount of evaporated liquid can be expressed as $g_h = \Theta A (x_s - x)$, where $g_h$=amount of evaporated water per hour (kg/h), $\Theta = (25+19 v)$=evaporation coefficient (kg/m2h), v=velocity of air above the water surface (m/s), A=water surface area (m2), $x_s$=maximum humidity ratio of saturated air at the same temperature as the water surface (kg/kg) (kg H2O in kg Dry Air)—constant in specific area, and x=air humidity ratio (kg/kg) (kg H2O in kg Dry Air). Accordingly, based on the volume of gel evaporated, the time passed since activation can be determined.

In aspects of the disclosure, gel 220, 320 can be formed from any suitable ingredients. For example, a medicinal ingredient may include 62% ethyl alcohol and non-medicinal ingredients may include aminomethyl propanol, aqua, carbomer, denatonium benzoate, glycerin, polysorbate20 and tocopheryl acetate. As another example, a slow-evaporating hydrophilic glycol ether may be used as a gel 220, 320 based timer, with 100% water solubility, good coalescing and coupling properties, a high dilution ratio and low viscosity.

Figure 11:
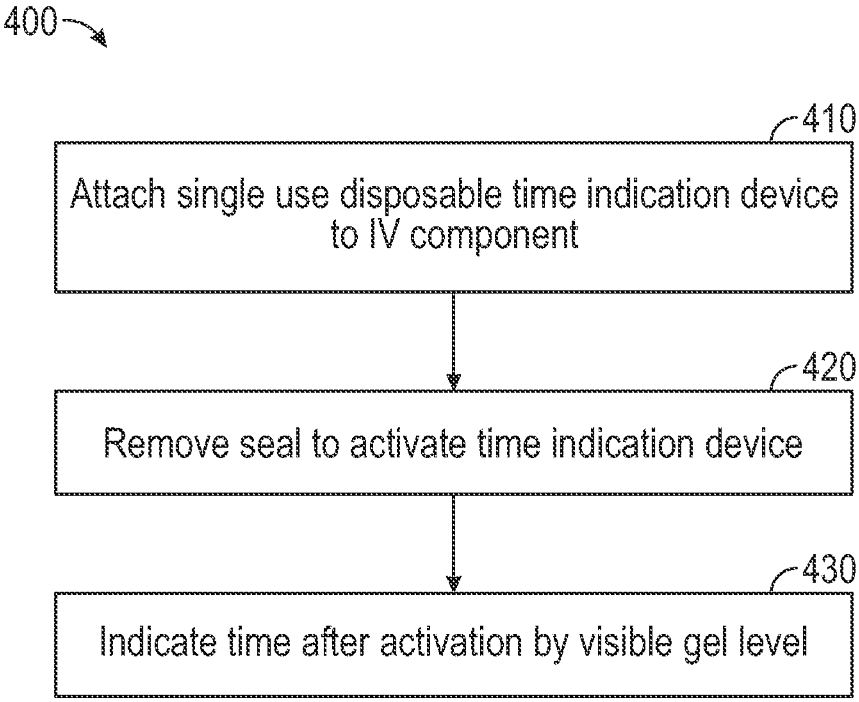
FIG. 11 illustrates a method of using a single use disposable time indication device, according to aspects of the disclosure.

According to some aspects of the disclosure, a method 400 of using a single use disposable time indication device is shown in FIG. 11. In step 410, a single use disposable time indication device (e.g., single use disposable time indication device 200, 300) is disposed on or attached to an IV set component (e.g., needleless connector 190). In aspects of the disclosure, the single use disposable time indication device may be an adhesive label or tag that is attached to (e.g., stuck to) the IV set component (e.g., IV tubing 160). In aspects of the disclosure, the single use disposable time indication device may be a cap that is threaded onto a connector (e.g., needleless connector 190).

A covering seal (e.g., seal 230, 330) is removed to activate the single use disposable time indication device in step 420. For example, a seal (e.g., seal 230) may be peeled off or removed from a tube (e.g., tube 210) containing a volume of gel (e.g., gel 220), thus exposing the gel to air. As another example, a seal (e.g., seal 330) may be peeled off or removed from a cap (e.g., cap 310) containing a volume of gel (e.g., gel 320), again exposing the gel to the air.

In step 430, the degree of gel evaporation from the single use disposable time indication device is viewable. For example, the volume of gel (e.g., gel 220, 320) reduces or recedes within a tube or slot (e.g., tube 210, slot 312) of the single use disposable time indication device (e.g., single use disposable time indication device 200, 300) over time. Time indicators (e.g., time indicators 240, 340) provide visual references of elapsed times associated with the level of gel remaining (e.g., gel level 250, 350) at any given time after activation.

In some embodiments according to the disclosure, an IV disposable time indication device comprises: a tube containing a volume of gel, wherein the gel is configured to evaporate at a determined rate of time upon activation by exposure to ambient air; a seal configured to prevent contact of the gel with ambient air; and one or more time indicators, wherein evaporation of the gel is configured to provide a visual indication of a passage of time after activation.

In aspects of the disclosure, the seal comprises vacuum sealed packaging containing the tube. In aspects of the disclosure, the seal comprises a removable cover disposed on an opening of the tube. In aspects of the disclosure, the one or more time indicators comprise one of word descriptions, numbers and symbols, each time indicator indicating a specific use time period. In aspects of the disclosure, an IV set comprises IV tubing, an IV component coupled to the IV tubing and an IV disposable time indication device coupled to one of the IV tubing and the IV component, the IV disposable time indication device comprising: a tube containing a volume of gel, wherein the gel is configured to evaporate at a determined rate of time upon activation by exposure to ambient air; a seal configured to prevent contact of the gel with ambient air; and one or more time indicators, wherein evaporation of the gel is configured to provide a visual indication of a passage of time after activation. In aspects of the disclosure, the IV disposable time indication device is disposed on a label and the label is coupled to one of the IV tubing and the IV component.

In some embodiments according to the disclosure, an IV disposable time indication device comprises: a cap configured to be coupled to an IV component, the cap comprising: a cavity having a base surface; a slot disposed in the base surface; a volume of gel disposed in the slot, wherein the gel is configured to evaporate at a determined rate of time upon activation by exposure to ambient air; and one or more time indicators; and a seal configured to prevent contact of the gel with ambient air, wherein evaporation of the gel is configured to provide a visual indication of a passage of time after activation.

In aspects of the disclosure, the cap further comprises a disinfecting substance disposed on an inner surface of the cap and configured to sterilize a surface of the IV component when the cap is coupled to the IV component. In aspects of the disclosure, the cap comprises internal threads configured to mate with external threads of the IV component. In aspects of the disclosure, the cap comprises: a tether coupled to the cap; and an engagement member coupled to the tether, wherein the engagement member is configured to be coupled to the IV component.

In aspects of the disclosure, a cap closer is configured to fit within the cavity, the cap closer comprising a surface configured to contact the base surface and to hold the gel within the slot. In aspects of the disclosure, the cap closer is formed of a material configured to provide a view of the gel within the slot, the material comprising one of a transparent material and a semi-transparent material. In aspects of the disclosure, the cap closer comprises a vent portion configured to provide an air passageway between the gel in the slot and ambient air. In aspects of the disclosure, the seal comprises a removable cover disposed on the cap and covering the vent portion. In aspects of the disclosure, the seal comprises vacuum sealed packaging containing the cap. In aspects of the disclosure, the one or more time indicators comprise one of word descriptions, numbers and symbols, each time indicator indicating a specific use time period.

In aspects of the disclosure, an IV set comprises IV tubing, an IV component coupled to the IV tubing and an IV disposable time indication device coupled to the IV component, the IV disposable time indication device comprising: a cap configured to be coupled to an IV component, the cap comprising: a cavity having a base surface; a slot disposed in the base surface; a volume of gel disposed in the slot, wherein the gel is configured to evaporate at a determined rate of time upon activation by exposure to ambient air; and one or more time indicators; and a seal configured to prevent contact of the gel with ambient air, wherein evaporation of the gel is configured to provide a visual indication of a passage of time after activation. In aspects of the disclosure, the IV component is a threaded needleless connector, and wherein the cap comprises threads and a disinfecting substance disposed on an inner surface of the cap, the cap configured to sterilize a connection surface of the needleless connector when the cap is screwed onto the needleless connector.

In some embodiments according to the disclosure, a method of operating an IV disposable time indication device comprises: placing an IV component into use for an IV infusion process; removing a seal from the IV disposable time indication device coupled to the IV component; exposing a gel within the IV disposable time indication device to ambient air; visually identifying a level of the gel relative to one or more time indicator markings disposed adjacent to the gel; and determining the remaining use life of the IV component based on the time indicator marking closest to the identified level of gel.

In aspects of the disclosure, the IV component is a threaded needleless connector and the IV disposable time indication device is a threaded cap screwed onto the threaded needleless connector, the threaded cap comprising: a cavity having a base surface; a slot disposed in the base surface; and a cap closer within the cavity, the cap closer comprising a surface covering the base surface and a vent portion providing an air passageway between the slot and ambient air, wherein the gel is disposed in the slot and evaporates at a determined rate of time upon removal of the seal.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, inserting and the like via a hardware element.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An intravenous (IV) disposable time indication device, comprising:

a tube having one open end and containing a volume of gel, wherein the gel is configured to evaporate from the open end at a determined rate of time upon activation by exposure to ambient air;

a seal configured to prevent contact of the gel with ambient air; and a plurality of time indicators disposed along a length of the tube, wherein evaporation of the gel is configured to provide a visual indication of a first passage of time after activation based on a first position of an end of the gel closest to the open end of the tube in relation to a first one of the the plurality of time indicators, and wherein further evaporation of the gel is configured to provide a visual indication of a second passage of time after activation based on a second position of an end of the further evaporated gel closest to the open end of the tube in relation to a second one of the plurality of time indicators.

2. The IV disposable time indication device of claim 1, wherein the seal comprises vacuum sealed packaging containing the tube.

3. The IV disposable time indication device of claim 1, wherein the seal comprises a removable cover disposed on an opening of the tube.

4. The IV disposable time indication device of claim 1, wherein the plurality of time indicators comprise one of word descriptions, numbers and symbols, each time indicator indicating a specific use time period.

5. An IV set, comprising:

IV tubing;

an IV component coupled to the IV tubing; and the IV disposable time indication device of claim 1 coupled to one of the IV tubing and the IV component.

6. The IV set of claim 5, wherein the IV disposable time indication device is disposed on a label and the label is coupled to one of the IV tubing and the IV component.

7. A method of operating the IV disposable time indication device of claim 1, the method comprising:

placing an IV component into use for an IV infusion process;

removing the seal from the IV disposable time indication device coupled to the IV component;

exposing the gel within the IV disposable time indication device to ambient air;

visually identifying a level of the gel relative to the plurality of time indicators disposed adjacent to the gel; and determining a remaining use life of the IV component based on the time indicator closest to the level of gel that is identified.

8. An intravenous (IV) disposable time indication device, comprising:

a cap configured to be coupled to an IV component, the cap comprising:

a cavity disposed in an end of the cap, the cavity having a base surface;

a slot disposed in the base surface;

a volume of gel disposed in the slot, wherein the gel is configured to evaporate at a determined rate of time upon activation by exposure to ambient air;

a cap closer disposed within the cavity, the cap closer comprising a surface disposed on the base surface, the cap closer configured to hold the gel within the slot and to provide an air passageway at a first end of the slot; and a plurality of time indicators disposed along a length of the slot; and a seal configured to prevent contact of the gel with ambient air, wherein evaporation of the gel is configured to provide a visual indication of a first passage of time after activation based on a first position of an end of the gel closest to the first end of the slot in relation to a first one of the the plurality of time indicators, and wherein further evaporation of the gel is configured to provide a visual indication of a second passage of time after activation based on a second position of an end of the gel that is further evaporated closest to the first end of the slot in relation to a second one of the plurality of time indicators.

9. The IV disposable time indication device of claim 8, wherein the cap further comprises a disinfecting substance disposed on an inner surface of the cap and configured to sterilize a surface of the IV component when the cap is coupled to the IV component.

10. The IV disposable time indication device of claim 8, wherein the cap comprises internal threads configured to mate with external threads of the IV component.

11. The IV disposable time indication device of claim 8, wherein the cap comprises:

a tether coupled to the cap; and an attachment member coupled to the tether, wherein the attachment member is configured to be coupled to the IV component.

12. The IV disposable time indication device of claim 8, wherein the cap closer is formed of a material configured to provide a view of the gel within the slot, the material comprising one of a transparent material and a semi-transparent material.

13. The IV disposable time indication device of claim 8, wherein the cap closer comprises a vent portion configured to provide an air passageway between the gel in the slot and ambient air.

14. The IV disposable time indication device of claim 13, wherein the seal comprises a removable cover disposed on the cap and covering the vent portion.

15. The IV disposable time indication device of claim 8, wherein the seal comprises vacuum sealed packaging containing the cap.

16. The IV disposable time indication device of claim 8, wherein the plurality of time indicators comprise one of word descriptions, numbers and symbols, each time indicator indicating a specific use time period.

17. An IV set, comprising:

IV tubing;

the IV disposable time indication device of claim 8 coupled to the IV component; and the IV component coupled to the IV tubing.

18. The IV set of claim 17, wherein the IV component is a threaded needleless connector, and wherein the cap comprises threads and a disinfecting substance disposed on an inner surface of the cap, the cap configured to sterilize a connection surface of the needleless connector when the cap is screwed onto the needleless connector.

19. A method of operating the IV disposable time indication device of claim 8, the method comprising:

placing the IV component into use for an IV infusion process;

removing the seal from the IV disposable time indication device coupled to the IV component;

exposing the gel within the IV disposable time indication device to ambient air;

visually identifying a level of the gel relative to the plurality of time indicators disposed adjacent to the gel; and determining a remaining use life of the IV component based on the time indicator closest to the level of gel that is identified.

* * * * *